Feb. 3 , 1953 H. A. M. VERSCHUREN Plant Pat. 1,164
ROSE PLANT
Filed Feb. 7, 1952
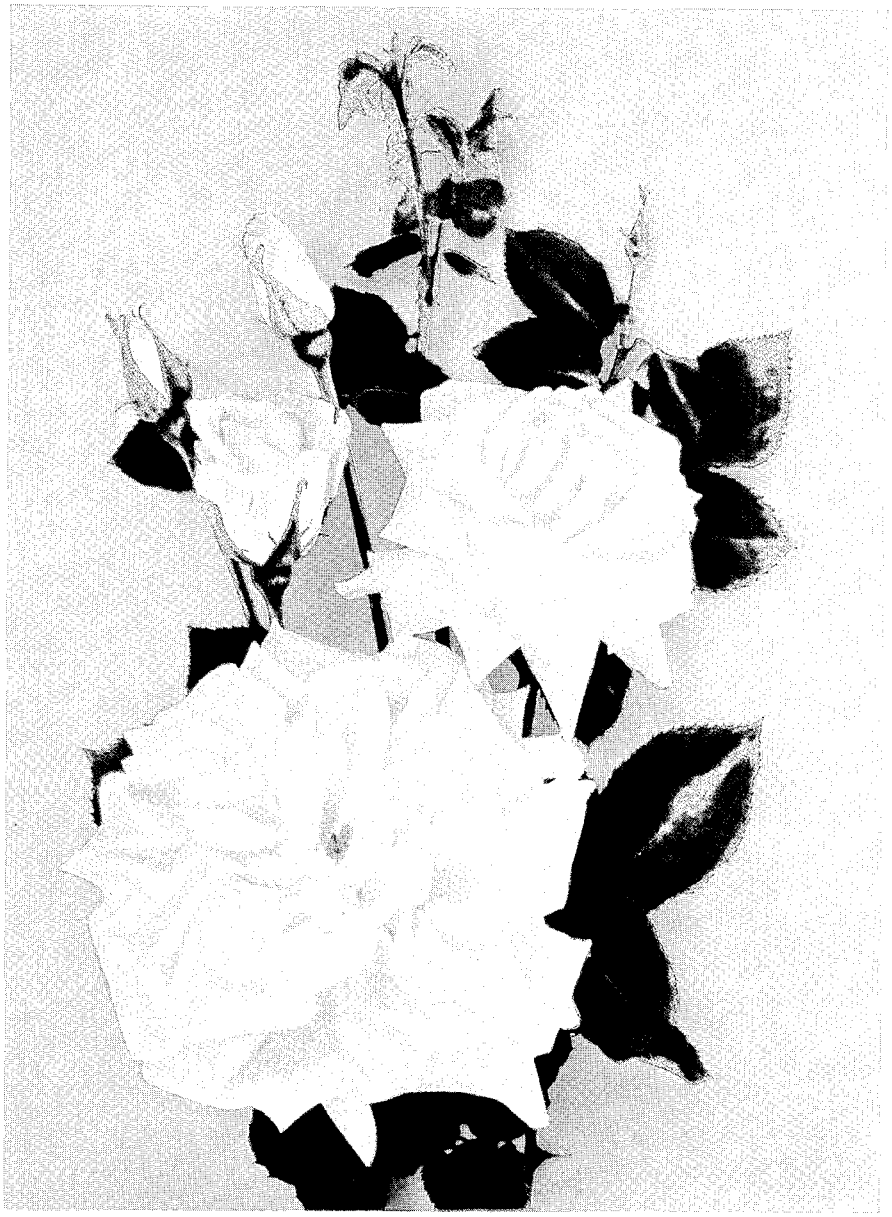
Inventor.
H. A. M. Verschuren
By: Robert Cobb
Attorneys.

Patented Feb. 3, 1953

Plant Pat. 1,164

UNITED STATES PATENT OFFICE 1,164

ROSE PLANT

Hendrikus Antonie Maria Verschuren, Haps, Netherlands, assignor to Jackson & Perkins Company, Newark, N. Y., a corporation of New York Application February 7, 1952, Serial No. 270,299

1 Claim. (Cl. 47—61)

The present invention relates to a new and distinct variety of rose plant of the hybrid tea class, originated by me by crossing the variety "Golden Scepter" (Plant Patent No. 910) × an unnamed and unpatented Deep Orange-Yellow seedling.

The objective of this cross was to improve and deepen the color of the flowers of "Golden Scepter." This objective was fully achieved, as evidenced by the fact that the color of the flowers of my new variety is substantially deeper and more outstanding than that of "Golden Scepter," and was attained without diminishing the strength and vigor of the plant.

My new variety is distinguished from its parents, as well as from all other varieties of its class, by the following unique and desirable combination of dominant features:

(1) The Light Orange-Yellow color of its flowers, shaded with Deep Chrome;

(2) The high-centered characteristic of its flowers;

(3) The increased petalage of its flowers, as compared with those of "Golden Scepter," without loss of productivity;

(4) The leathery, Dark Cress Green color of its foliage; and (5) The general similarity of its thorns and foliage to those of "Golden Scepter."

Asexual reproduction of my new variety by budding at Newark, New York, and at Pleasanton, California, U. S. A., shows that the foregoing characteristics and distinctions come true to form, and are established and transmitted through succeeding propagations.

The accompanying drawing shows specimens of my new variety, with the flowers and foliage depicted in typical color and in different stages of development.

The following is a detailed description of my new variety, with color terminology in accordance with Ridgway's Color Standards and Nomenclature:

Parentage: Seedling.

*Seed parent.*—"Golden Scepter."

*Pollen parent.*—An unnamed Deep Orange-Yellow seedling.

Classification: Botanic and commercial—hybrid tea.

Propagation: Holds its distinguishing characteristics through succeeding propagations by budding.

*Flower*

(Observations made in the greenhouse at Newark, New York, in the late morning, early in the month of September.)

Blooming habit: Recurrent—continuous.

Bud:

*Size.*—Large.

*Form.*—Pointed; is not affected by wet or hot weather.

*Color.*—When sepals first divide—Capucine Yellow, Plate 3. When petals begin to unfurl—Light Orange-Yellow, Plate 3, lightly overcast with Capucine Orange, Plate 3. When half blown: inside of petals—Deep Chrome, Plate 3; reverse of petals—Orange Buff, Plate 3.

*Sepals.*—Branched; curl back when petals begin to unfurl. Color: inside—Kildare Green, Plate 31; outside—Light Bice Green, Plate 17.

*Calyx.* — Shape — apple. Size — broad. Aspect—smooth. Odor when rubbed—none. Color—Light Bice Green, Plate 17.

*Peduncle.* — Length — medium. Aspect — smooth. Strength—erect; slender. Color—Lettuce Green, Plate 5.

*Opening.*—Opens up well; is not affected by adverse weather conditions.

Bloom:

*Size.*—Large. Average size when fully expanded, 4½ inches to 5 inches.

*Borne.*—Singly.

*Stems.*—Medium length; normal strength.

*Form.*—When first open—high center. Permanence—retains its form to the end, but flattens somewhat; some petals stay upright and give it a graceful, irregular appearance.

*Petalage.*—Double (full but open center). Number of petals under normal conditions, 45 to 50.

*Color.*—Center of flower—Deep Chrome, Plate 3. Outer petals—Light Orange Yellow, Plate 3. Base of petals (aiglet)—Lemon Chrome, Plate 4. Inside of petals—Light Orange Yellow, Plate 3, shaded with Deep Chrome, Plate 3. Reverse of petals—Pinard Yellow, Plate 4, overcast with Pale Orange Yellow, Plate 3. General tonality from a distance—Light Orange Yellow, Plate 3.

*Discoloration.*—General tonality at end of first day—Light Orange Yellow, Plate 3, shaded with Deep Chrome, Plate 3. Second day—Light Orange Yellow, Plate 3. Third day—Pale Orange Yellow, Plate 3.

Petals:

*Texture.*—Leathery; is not affected by wet or hot weather.

*Appearance.* — Inside — velvety; outside — satiny.

*Form.*—Oval.

*Arrangement.*—Informal (with "rags" in center). Petaloids in center—few; large.

*Persistence.*—Drop off cleanly.

*Fragrance.*—Moderate. Nature—tea (average hybrid tea scent).

*Lasting quality.*—On the plant and as cut flower—long.

*Genital organs*

Stamens, anthers: Medium size; many.

*Arrangement.*—Regular around styles.

*Color.*—Deep Chrome, Plate 3.

Stamens, filaments (threads):

*Length.*—Long.

*Color.*—Lemon Chrome, Plate 4.

Pollen: Color—Pale Orange Yellow, Plate 3.

Styles: Columnar; uneven length; short; thin.

Stigmas: Color—Sulphur Yellow, Plate 5.

Ovaries: All enclosed in calyx.

*Plant*

Form: Bush.

Growth: Vigorous; upright.

Foliage: 5 to 7 leaflets.

*Size.*—Medium.

*Quantity.*—Normal abundance.

*Color.*—New Foliage: upper side—Lettuce Green, Plate 5; edges and serrations Mahogany Red, Plate 2; under side—Cosse Green, Plate 5, overcast with Mahogany Red, Plate 2. Old foliage: upper side—Dark Cress Green, Plate 31; serrations Carmine, Plate 1; underside—Light Cress Green, Plate 31; serrations Carmine, Plate 1.

*Shape.*—Oval pointed.

*Texture.* — Upper side—leathery. Under side—smooth. Ribs and veins—ordinary.

*Edge.*—Serrated (saw toothed).

*Serration.*—Double; sharp.

*Leaf stem.*—Color—Absinthe Green, Plate 31. Under side—prickles.

*Stipules.*—Medium length; smooth.

Wood:

*New wood.*—Color—Lettuce Green, Plate 5. Bark—smooth.

*Old wood.*—Color—Forest Green, Plate 17. Bark—smooth.

Thorns:

*Thorns.*—Quantity—on main stalks from base and on laterals from stalk—ordinary. Form — narrow base; medium length; hooked downward. Color when young—Carmine, Plate 1. Position—irregular.

*Prickles.*—On main stalks and on laterals—none.

*Short needles.*—On main stalks and on laterals—none.

I claim:

A new and distinct variety of rose plant of the hybrid tea class, substantially as herein shown and described, particularly characterized as to novelty by the Light Orange-Yellow color, with shadings of Deep Chrome, of its flowers, by the high-centered and increased petalage characteristics of its flowers, by the leathery, Dark Cress Green color of its foliage, and by the general similarity of its thorns and foliage to those of its parent "Golden Scepter" (Plant Patent No. 910).

HENDRIKUS ANTONIE MARIA VERSCHUREN.

No references cited.